US006451565B1

(12) United States Patent
Rabenhorst et al.

(10) Patent No.: US 6,451,565 B1
(45) Date of Patent: Sep. 17, 2002

(54) **METHOD OF PRODUCING γ-DECALACTONE USING *YARROWIA LIPOLYTICA* STRAIN HR 145 (DSM 12397)**

(75) Inventors: Jürgen Rabenhorst; Ian Gatfield, both of Höxter (DE)

(73) Assignee: Haarmann & Reimer GmbH, Holzminden (DE)

(*) Notice: Subject to any disclaimer, the term of this patent is extended or adjusted under 35 U.S.C. 154(b) by 0 days.

(21) Appl. No.: 09/830,148
(22) PCT Filed: Oct. 20, 1999
(86) PCT No.: PCT/EP99/07950
§ 371 (c)(1),
(2), (4) Date: Apr. 20, 2001
(87) PCT Pub. No.: WO00/24920
PCT Pub. Date: May 4, 2000

(30) Foreign Application Priority Data

Oct. 24, 1998 (EP) .............................. 98120206

(51) Int. Cl.$^7$ ............................. C12N 1/00; C12N 1/02; C12P 7/24; C12P 7/26; C12P 17/06
(52) U.S. Cl. ...................... 435/125; 435/147; 435/148; 435/252.1; 435/255.1; 435/261; 435/911
(58) Field of Search ..................... 435/41, 52, 124, 435/147, 252.1, 255.1, 260, 261, 911, 125, 148

(56) References Cited

U.S. PATENT DOCUMENTS 4,560,656 A * 12/1985 Farbood et al. ............. 435/146
5,215,901 A * 6/1993 Boog et al. ................. 435/125

FOREIGN PATENT DOCUMENTS

DE   4126997   2/1993
DE   2734843   12/1996

OTHER PUBLICATIONS

*Chemical Abstracts, vol. 121, No. 25, Dec. 19, 1994, columbus, Ohio, US; abstract No. 295696, Morgunov, I.G. et al: "Isolation, purification and some properties of citrate synthase from citric acid–accumulating yeast *Yarrowia* (Candida) *lipolytica*" XP002105356 & Biokhimiya (Moscow) (1994), 59(9), 1320–9 Coden: Biohao:ISSN: 0320–9725.

*Chemical Abstracts, vol. 122, No. 21, May 22, 1995, Columbus, Ohio, US; Abstract No. 263911 Gatfield, I. L. et al: "The enzymatic and fermentative production of lactones and their use in natural flavors" XP002105362 & Recent Dev. Flavor Fragrance Chem., Proc. Int. Haarmann Reimer Symp., 3$^{rd}$ (1993), 291–304. Editor(s): Hopp, Rudolf; Mori, Kenji. Publisher: VCH, Weinheim, Germany. Coden: 60zgah.

*Chemical Abstracts, vol. 121, No. 19, Nov. 7, 1994, Columbus, Ohio, US; Abstract No. 229299, Gatfield, I.L. et al: "Aspects of the microbiological manufacture of flavor–active lactones with particular reference to gamma.–declactone" XP002105363 & Chem., Mikrobiol., Technol. Lebensm. (1993), 15(5/6), 165–70 Coden: CMTLBX;ISSN; 0366–7154.

*Chemical Abstracts, vol. 127, No. 17, Oct. 27, 1997, Columbus, Ohio, US; Abstract No. 233574, Pagot, Y. et al: "Utilization of an auxotrophic strain of the yeast Yarrowia Lipolytica to improve. gamma.–decalactone production yields" XP002105364 & Lett. Appl. Microbiol. (1997), 25(2), 113–116 Coden: Lamie7;issn: 0266–8254.

* cited by examiner

Primary Examiner—David M. Naff
Assistant Examiner—Deborah K. Ware
(74) Attorney, Agent, or Firm—Joseph C. Gil; Noland J. Cheung; Jennifer R. Seng

(57) ABSTRACT

A process is provided for producing γ-decalactone using *Yarrowia lipolytica* HR 145 (DSM 12397). The process includes preparing the product in a bioreactor by culturing the pure strain of *Yarrowia lipolytica* in a culture medium containing carbon compounds, nitrogen compounds, inorganic salts, trace elements, vitamins, etc. Other ingredients of the culture medium include glycerol, glucose, mannitol, citric acid, malt extract, yeast extract, casein hydrolysate, castor oil, cotton seed meal or corn steep liquor. Also sulphates, nitrates, chlorides, carbonates or phosphates of metals sodium, potassium magnesium, manganese, calcium, zinc, and mixtures thereof can be used in the culture medium. Further, a pure strain of *Yarrowia lipolytica* HR 145 (DSM 12397) is provided.

14 Claims, No Drawings

METHOD OF PRODUCING γ-DECALACTONE USING *YARROWIA LIPOLYTICA* STRAIN HR 145 (DSM 12397)

FIELD OF THE INVENTION

The present invention relates to a novel process for preparing γ-decalactone.

BACKGROUND OF THE INVENTION

γ-Decalactone, owing to its organoleptic properties, is an important aroma compound which has a fruity, peach-like flavour and aroma. In principle, γ-decalactone can be produced from fruits. However, it is present in these in such small amounts that it cannot be isolated economically by extraction or distillation.

Therefore, in recent years there have been numerous attempts to prepare γ-decalactone in biotechnological processes. Most of the processes operate with the use of various yeasts. In this case, either castor oil or the methyl ester of the ricinoleic acid isolated therefrom is converted by the yeasts. The yields achieved in this process vary between a few milligrams per litre up to 9.4 g/l in 75 hours (FR 2 734 843).

The process has, in addition, the disadvantage that a uracil-auxotrophic material is employed and thus two separate steps are necessary for the biomass formation and production.

SUMMARY OF THE INVENTION

The objection of the present invention is therefore to provide a process which makes The object of the present invention is therefore to provide a process which makes higher yields possible higher yields possible.

This object is achieved by means of the fact that a culture comprising *Yarrowia lipolytica* is used.

DETAILED DESCRIPTION OF THE INVENTION

It is possible according to the invention to use *Yarrowia lipolytica* in a mixture with other microorganisms. However, preferably, *Yarrowia lipolytica* is used as a pure culture. Particular preference is given according to the invention to culturing the strain *Yarrowia lipolytica* HR 145 (DSM 12397).

A biologically pure culture of strain *Yarrowia lipolytica*, HR 145 (DSM 12397), was deposited on Aug. 26, 1998, under the terms of the Budapest Treaty at the DSMZ-Deutsche Sammiung Von Mikroorganismen Und Zellkulturen GmbH in Braunschweig under the number DSM 12397.

As substrate for the culture used according to the invention, synthetic, semisynthetic or complex culture media can be used. These comprise carbon compounds and nitrogen compounds, inorganic salts with or without trace elements and vitamins.

As carbon compounds, carbohydrates, hydrocarbons or organic base chemicals can preferably be used. Examples of compounds which can preferably be used are sugars, alcohols and/or sugar alcohols, organic acids or complex mixtures. According to the invention, preference is given to oils.

As sugar, glucose is preferably used. The useable alcohols preferably include glycerol or mannitol. Organic acids which can be used are preferably citric acid. Complex mixtures include, for example, malt extract, yeast extract, casein or casein hydrolysate. As oil, in particular castor oil is useable. In these cases, according to the invention, mixtures of two or more of the said compounds can be used.

As nitrogenous substrates, inorganic compounds can be used. Examples of these are nitrates and ammonium salts. Likewise, organic nitrogen sources can be used. These include yeast extract, soya flour, cotton seed meal, casein, casein hydrolysate, wheat gluten and corn steep liquor. It is also possible to use two or more of the said compounds as a mixture.

The inorganic salts which can be used include, for example, borates, carbonates, chlorides, molybdates, nitrates, phosphates and sulphates. As metals, the said salts preferably contain calcium, iron, potassium, cobalt, copper, magnesium, manganese, sodium or zinc. According to the invention, a mixture of two or more of the said salts can also be used.

The temperature for the culture is preferably in the range from 10 to 40° C. Particular preference is given to the range from 20 to 35° C., very high preference is given to 25 to 30° C.

The pH of the medium is preferably 4 to 9. Particular preference is given to the range from 5 to 8.

During the production process, adequate aeration is necessary. The reactors which can be used according to the invention are to be designed accordingly. In principle, according to the invention, all bioreactors suitable for aerobic processes and known to those skilled in the art can thus be used. Preferably, all apparatuses suitable for any aerobic submerged process can be used. That is to say, vessels without or with a mechanical mixing device can be used according to the invention. The former include, for example, shaking apparatus, bubble-column reactors or loop reactors. The latter preferably include all known apparatuses having stirrers in any design.

The process according to the invention can be carried out continuously or batchwise. The fermentation time until a maximum amount of product is reached is in the range from 36 to 72 hours, preferably in the range from 48 to 66 hours, calculated from inoculation of the culture.

According to the invention, the substrates can be added at the beginning of the incubation, during growth or after completion of growth. This can be achieved by a single addition of substrates or by continuous successive addition during the process.

However, preference is given to continuous addition over a period of a plurality of hours after inoculation of the culture.

Using the processes described according to the invention it is surprisingly possible to produce more than 11 g/l of γ-decalactone in less than 70 hours. The invention and associated surprising findings are described in more detail by the following examples.

EXAMPLES

1. Preparation of the Preliminary Culture 1.7 g of malt extract are dissolved in 100 ml of water in a 500 ml conical flask having a side insert and the solution was sterilized in an autoclave at 121° C. for 15 minutes. After cooling to room temperature, the malt broth flask is inoculated using an inoculation loop from a slope culture of *Yarrowia lipolytica* HR 145. The flask is incubated for 24 hours on a rotary shaking machine at 27° C. and 100 rpm.

Two 500 ml conical flasks having a side insert are charged with medium (1.461 g of $Na_2HPO_4 \times 12\ H_2O$; 0.352 g of $KH_2PO_4$; 0.53 g of urea; 0.07 g of Tween 80; 5 g of yeast powder; 1 g of castor oil and 100 ml of water) and are sterilized in an autoclave at 121° C. for 15 minutes. After cooling to room temperature, each of the flasks is inoculated with 500 gl of a malt extract broth culture of *Yarrowia lipolytica* HR 145.

The flasks are incubated for 24 hours on the rotary shaking machine at 27° C. and 100 rpm.

2. Production of γ-Decalactone in the 10l Fermenter 9.8l of water are charged into the fermenter and 14.61 g of $Na_2HPO_4 \cdot 12H_2O$, 53 g of urea, 50 g of $MgSO_4 \cdot 7H_2O$, 0.04 g of riboflavin, 500 g of yeast powder, 7.0 g of Tween 80, 100 g of castor oil and 5 g of antifoam are added. The medium is sterilized in situ at 121° C. for 30 minutes. In addition, 500 g each of dilute sodium hydroxide solution and sulphuric acid as well as castor oil are sterilized in the autoclave. After cooling, the antifoam probe and the tapping fitting for NaOH are attached. The pH after sterilization is about pH 7.9. By means of dilute sulphuric acid a pH of 7.0 is established. The stirring speed is 400 rpm; the aeration is 3 l/min of compressed air; the temperature is 27° C.

The fermenter is inoculated with the preliminary culture via a sterile tapping fitting. During the fermentation, further sodium hydroxide solution is added to keep the pH at pH 7.0. Defoamer is added automatically as required. 14 hours after the inoculation, substrate addition is started. 500 g of castor oil are added in the course of 4 hours.

After a fermentation time of approximately 52 hours, the fermentation is ended. The time to stop the fermentation is reached when no more sodium hydroxide solution has been added for one hour. To stop the fermentation, the fermenter contents are set to pH 2.0 using concentrated sulphuric acid and heated to 80° C. for 30 minutes. After cooling, the contents are racked off for the subsequent work up. The final ydecalactone concentration, according to HPLC, is 11,500 to 12,500 ppm. The ratio of 3-hydroxy-γ-decalactone to γ-decalactone is less than 0.2.

From the resultant culture broth, if appropriate after centrifugation, the γ-decalactone is then isolated by the known physical processes (distillation, extraction etc.).

3. Production on a 300 l Scale 200 ml of preliminary culture were prepared precisely as described in Example 1 and used to inoculate a 300 l fermenter. 140 l of water were previously charged into the fermenter and 742 g of urea, 49 g of $KH_2PO_4$, 12 g of $H_2O$, 7 g of yeast extract and 98 g of Tween 80 added. The medium is sterilized in situ at 121° C. for 30 minutes.

After cooling, the antifoam probe and the tapping fitting for NaOH are attached. The pH after sterilization is about 7.0. The stirrer speed is set to 180 rpm, the aeration to 35 l/min and the temperature to 27° C. The fermenter is inoculated under sterile conditions with the 200 ml of preliminary culture. During the fermentation, the pH is kept constant at 7.0 using sodium hydroxide solution. About 16 hours after the inoculation, addition of castor oil (7.4 kg) is started, and completed after a further 4 hours.

After a fermentation time of 69 hours, the fermentation is ended. The final concentration of γ-decalactone is 12.3 g/l. The ratio of 3-hydroxy-γ-decalactone to γ-decalactone is 0.125, since only 1.53 g/l of 3-hydroxy-γ-decalactone are formed.

What is claimed is:

1. A biologically pure culture of strain *Yarrowia lipolytica* HR 145 (DSM 12397).

2. Process for preparing γ-decalactone in a bioreactor, comprising culturing a biologically pure culture of strain *Yarrowia lipolytica* HR 145 (DSM 12397).

3. Process according to claim 2, wherein culture medium is a synthetic or semisynthetic.

4. Process according to claim 2, wherein the culture medium comprises carbon compounds nitrogen compounds, inorganic salts, trace elements and/or vitamins.

5. Process according to claim 4, wherein carbon compounds are sugars, sugar alcohols, alcohols, organic acids, oils or mixtures there of.

6. Process according to claim 5, wherein the culture medium comprises glucose, glycerol, mannitol, citric acid, malt extract, yeast extract, casein, casein hydrolysate, castor oil or mixtures there of.

7. Process according to claim 2, wherein the culture medium comprises inorganic compounds and/or organic compounds.

8. Process according to claim 7, wherein the culture medium comprises nitrates, ammonium salts, yeast extract, soya flour, cotton seed meal, casein, casein hydrolysate, wheat gluten or corn steep liquor.

9. Process according to claim 2, wherein the culture medium comprises sulphates, nitrates, chlorides, carbonates or phosphates of the metals sodium, potassium, magnesium, manganese, calcium, zinc or iron or mixtures there of.

10. Process according to claim 2, wherein said culturing is at a temperature in the range from 10 to 40° C.

11. Process according to claim 10, wherein the temperature is in the range from 20 to 300° C.

12. Process according to claim 2, wherein the culture medium has a pH in the range from 4 to 11.

13. Process according to claim 12, wherein the pH is in the range from 5 to 8.

14. Process according to claim 2, wherein said culturing produces both hydroxy-γ-decalactone and γ-decalactone a ratio of hydroxyn-γ-decalactone to γ-decalactone of less than or equal to 0.25 in the culture medium.

* * * * *